US006914959B2

(12) United States Patent
Bailey et al.

(10) Patent No.: US 6,914,959 B2
(45) Date of Patent: Jul. 5, 2005

(54) COMBINED RADIATION THERAPY AND IMAGING SYSTEM AND METHOD

(75) Inventors: Eric M. Bailey, Hampton, NH (US); Andrew P. Tybinkowski, Boxford, MA (US); George Harootian, Jr., Worcester, MA (US); Lidia Nemirovsky, Salem, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 10/215,546

(22) Filed: Aug. 9, 2002

(65) Prior Publication Data

US 2003/0048868 A1 Mar. 13, 2003

Related U.S. Application Data

(60) Provisional application No. 60/311,240, filed on Aug. 9, 2001.

(51) Int. Cl.[7] .............................. A61N 5/10; H05G 1/60

(52) U.S. Cl. ................. 378/65; 378/5; 378/9; 378/41; 378/98.9

(58) Field of Search ........................... 378/5, 9, 41, 57, 378/65, 68, 92, 98.9

(56) References Cited

U.S. PATENT DOCUMENTS

| | | | | |
|---|---|---|---|---|
| 5,490,196 A | * | 2/1996 | Rudich et al. | 378/101 |
| 5,661,773 A | * | 8/1997 | Swerdloff et al. | 378/65 |
| 5,724,400 A | * | 3/1998 | Swerdloff et al. | 378/65 |
| 5,751,781 A | * | 5/1998 | Brown et al. | 378/65 |
| 6,173,033 B1 | * | 1/2001 | Klingenbeck-Regn et al. | 378/20 |
| 6,198,790 B1 | * | 3/2001 | Pflaum | 378/9 |
| 6,370,223 B1 | * | 4/2002 | Gleason et al. | 378/58 |
| 6,385,288 B1 | * | 5/2002 | Kanematsu | 378/65 |
| 6,421,412 B1 | * | 7/2002 | Hsieh et al. | 378/9 |
| 2004/0024300 A1 | * | 2/2004 | Graf | 600/407 |

* cited by examiner

*Primary Examiner*—Allen C. Ho
(74) *Attorney, Agent, or Firm*—McDermott Will & Emery LLP

(57) ABSTRACT

A method of and system for locating a targeted region in a patient uses a CT imaging subsystem and a radiotherapy subsystem arranged so the targeted region can be imaged with the imaging system and treated with a beam of therapeutic X-ray radiation using a radiotherapy subsystem. The beam of therapeutic X-rays is in a plane that is substantially fixed relative to, and preferably coplanar with, a slice plane of the CT imaging subsystem so that the targeted region can be imaged during a planning phase, and imaged and exposed to the therapeutic X-rays during the treatment phase without the necessity of moving the patient.

23 Claims, 3 Drawing Sheets

COMBINED RADIATION THERAPY AND IMAGING SYSTEM AND METHOD

CROSS REFERENCE TO RELATED APPLICATIONS

This application is based on a provisional application, U.S. Ser. No. 60/311,240 filed Aug. 9, 2001.

REFERENCED PRIOR ART

U.S. Pat. No. 6,104,778, (Murad), X-ray Treatment and Apparatus; U.S. Pat. No. 5,692,507, (Seppi et al.) Computer Tomography Apparatus Using Image Intensifier Detector.

BACKGROUND

This disclosure relates to a system for and method of delivering radiotherapy using a x-ray beam for treatment. More particularly, this disclosure relates to a system for and method of determining the location of a particular target region within the body by using imaging techniques that help insure concentrated, high energy radiation is delivered only to the target region, and delivering the radiation so that it is concentrated only on the target region irrespective of patient movement during treatment.

In radiotherapy, for example as practiced in x-ray oncology, it is essential to deliver a precise amount of radiation, or dose, to a precisely defined, predetermined region of a patient's body. Because high levels of high energy radiation are used during radiation therapy treatment it is important that the therapist be able to precisely locate the site to be treated. Before a high-energy treatment machine is used to actually deliver the required radiation for treatment it has been known to use a low-energy imaging machine preliminarily to determine exactly where the dose should be delivered and how it can be achieved. For example, radiation therapists often attempt to use scans from diagnostic CT scanners in planning a radiation therapy treatment. However, in the prior art the relative position of organs within the body during a diagnostic CT scan are not the same as when a patient is placed on a flat couch of the radiation therapy machine. This occurs because the diagnostic CT scanner couch is usually more crescent shaped in cross section than the flat couch of the radiation therapy so that the soft tissue of the patient's body can shift.

Further, standard diagnostic CT scanners tend to be relatively expensive. Therefore, radiation therapy simulators have come into use for initially imaging the target region and its surrounds prior to therapy. A radiation therapy simulator is a diagnostic imaging X-ray machine shaped to simulate the geometry of radiation therapy (or radiotherapy) treatment units, and is typically cheaper than a standard CT scanner. A simulator includes an X-ray imaging source, a gantry to support and position the X-ray imaging source, a couch to support the patient, and an image forming system. The dimensions of the gantry are such that it positions the x-ray imaging source relative to the couch in a geometry mathematically similar to the geometry of the radiotherapy machine. More precisely, the X-ray focal spot for fluoroscopic/radiographic imaging by the simulator is positioned to allow the same target-to-patient isocenter (relative to the X-ray source and imaging detector) as in the radiotherapy machine, even though it is a separate machine. Images formed on the simulator can then be interpreted in terms of the geometry of the radiotherapy machine. Images can be taken from different angles to aid in the planning of how to form and direct the radiotherapy beam to maximize the dose (and exposure time) to the target and minimize damage to healthy organs.

These simulators also have patient couches that are identical to couches of radiation therapy machines.

Beam shaping devices and other accessories can be added to the simulator which attempt to exactly duplicate the therapy setup. Thus, simulators yield a projected planar image of the patient anatomy that is much more geometrically compatible with the position of the radiation therapy system.

In addition to the properly oriented radiographic information, if cross-sectional CT images could be obtained at the same time, then the therapist would be further aided in planning the treatment.

Computed Tomography Simulators

In existing simulators, because the geometry of the simulator attempts to very closely simulate that of the radiotherapy machine, the X-ray imaging source and image forming system are limited to a configuration which is less than optimal for the quality of the image. Both the source and the image-detector-part of the image forming system of the simulator are far from the patient.

An image intensifier has been used to increase the brightness of the image that can be used to produce a television image. A computer has been used to process and enhance the television image.

In the prior art, it is known to form a computed tomography image based on data obtained from a TV camera using an image intensifier tube (IIT) between the patient and a television camera. The output signal from the television camera is processed to form a digital signal that is further processed in a computer to form a tomographic image. This prior art system employing the television camera produces a noisy image of marginal value in simulation and planning.

Similar attempts have been made in the past by various groups to create CT images using X-ray image intensifiers with video cameras. However, from prior CT imaging experience, it is believed that the use of video camera signals based on data off the IIT was one of the major limiting features in these designs. Compared to the IIT, conventional video cameras have horizontal spatial resolution that can produce images with adequate resolution, but their intensity output is both limited and nonlinear. Typically, the instantaneous signal dynamic range of the video camera tube is limited to only two or three orders of magnitude. Conventional solid state video cameras have good linearity, spatially and in intensity, but their signal dynamic range is also limited.

A low cost, computer tomography system designed to be a computer tomography simulator for radiotherapy treatment planning is disclosed in U.S. Pat. No. 5,692,507.

Generally, after the shape and location of target region has been determined with a simulator, but before the patient is actually treated by the high-energy machine, a scheme must be established to deliver the high-energy radiation to the target region. The scheme usually involves determining the dose level and direction of the radiation beam. This includes determining how the beam should be collimated, or shaped, and directed, from different angles such that the predetermined dose will be accurately directed to the predetermined target region. Thus, once the shape and location of the target region is determined from each of multiple angles, the therapeutic beam can be shaped, typically using a multi-leaf collimator, to match the exposed target region from each respective direction of propagation of the beam, and directed at the tumor for treatment. This scheme can be followed at various angles.

The major problem with simulators is that once the target region is determined for the patient with the simulator, the patient is positioned at some later time in a separate radiotherapy machine for subsequent treatment. Often, as much as seven days is required between the planning phase and the treatment phase in order to determine maximum delivery to the target region from the information obtained from the simulator.

Various techniques have been designed to try to ensure that the therapeutic radiotherapy beam is properly shaped and delivered to the target region at each delivery angle. One approach is to place a tight outer garment (such as a corset), with indicia markings, on a patient around the area of the target region. The markings are visible in the images created by the simulators so that the targeted regions can be identified with reference to markings on the garments. An identical garment is worn by the patient during the treatment phase so that the target region can be identified by reference to the markings.

Another approach has been suggested in U.S. Pat. No. 6,104,778, wherein a laser light source is used as a surface marker to help direct the high energy therapeutic radiotherapy beam to the targeted region.

Even the slightest error in positioning the patient relative to the therapeutic high-energy beam of the radiation therapy machine, or movement of the patient while being treated, can displace the target region such that when the therapeutic radiation beam is delivered, it unnecessarily exposes healthy tissue, and partially or completely misses the target region.

SUMMARY OF THE INVENTION

In accordance with one aspect of the invention a combined system for planning and delivering X-ray therapy to a patient, the system includes:

a CT imaging subsystem defining at least one slice plane so that data generated by the CT imaging subsystem can be used to create images relative to the slice plane so that a target region of the patient can be (a) determined for treatment during a planning phase and (b) imaged during treatment during a treatment phase, and a radiation therapy subsystem for delivering a beam of therapeutic X-rays to the target region of the patient during treatment;

wherein the radiation therapy subsystem provides the beam of the therapeutic X-rays in a direction which is in a plane that is substantially fixed relative to the slice plane of the CT imaging system so that the targeted region can be imaged, and exposed to the beam of therapeutic X-rays without the necessity of moving the patient.

Preferably the radiation therapy subsystem provides the therapeutic X-rays in a direction within a plane that is substantially coplanar with the slice plane of the CT imaging system so that the targeted region can be imaged, and exposed to the therapeutic X-rays without the necessity of moving the patient.

The preferred radiation therapy subsystem includes a detector for detecting the radiation level of the beam; a collimator subsystem for shaping and sizing the beam of therapeutic X-rays; a support for pivoting a source of the beam of therapeutic X-rays so that the beam can be directed from a predetermined angle; the CT imaging system is adapted to provide stationary views (non-rotating gantry); the CT imaging system includes at least two sources of X-rays or a moving electron beam source; the two sources can be used to create a stereoscopic image of the target region; the two sources can be used to create a three-dimensional image when separated in the Z-axis; the two sources can be used to create separate images of the target region; the two sources can be used to create dual energy beams of X-ray radiation; further includes a subsystem for automatically comparing images created during the planning and treatment phases; and further includes a patient table for use in both the planning and treatment phases, wherein the table is adjustable in three orthogonal directions.

In accordance with another aspect of the invention, a method of locating a targeted region in a patient using a CT imaging subsystem, and treating the targeted region with therapeutic X-ray radiation using a radiotherapy subsystem, comprises:

providing the therapeutic X-rays in a direction which is substantially fixed relative to a slice plane of the CT imaging subsystem so that the targeted region can be imaged during a planning phase, and imaged and exposed to the therapeutic X-rays during the treatment phase without the necessity of moving the patient.

In the preferred method the therapeutic beam provides the therapeutic X-rays in a direction within a plane that is substantially fixed relative to a slice plane of the CT imaging subsystem so that the targeted region can be imaged during a planning phase, and imaged and exposed to the therapeutic X-rays during the treatment phase without the necessity of moving the patient.

In accordance with another aspect of the invention, a method of planning and delivering X-ray therapy to a patient, comprises:

defining at least one slice plane of a CT imaging subsystem so as to create images relative to the slice plane so that a target region of the patient can be (a) determined for treatment during a planning phase and (b) imaged during treatment during a treatment phase, and delivering a beam of therapeutic X-rays to the target region of the patient during the treatment phase;

wherein the beam of the therapeutic X-rays is delivered in a direction which is in a plane that is substantially fixed relative to the slice plane so that the targeted region can be imaged, and exposed to the beam of therapeutic X-rays without the necessity of moving the patient.

The preferred method delivers the beam in a direction which is in a plane that is substantially coplanar within the slice plane so that the targeted region can be imaged, and exposed to the therapeutic X-rays without the necessity of moving the patient; detecting the radiation level of the beam with a detector subsystem; further adjusting the shape and size of the beam of therapeutic X-rays with a collimator subsystem; further including pivoting a source of the beam of therapeutic X-rays so that the beam can be directed from a predetermined angle; further including forming stationary views with the CT imaging system during the treatment phase; further including using at least two sources of X-rays to form the stationary views; further including using the two sources to create a stereoscopic image of the target region; further including using the two sources to create separate images of the target region during the planning phase; further including creating dual energy beams using the two sources; further including automatically comparing images created during the planning and treatment phases; further including using a patient table for both the planning and treatment phases; further including adjusting the table, as necessary in each of three orthogonal directions.

DETAILED DESCRIPTION OF THE DISCLOSURE

In general, the system combines a CT X-ray imaging system for providing the functionality of the simulator, and a high energy radiotherapy machine. The X-ray imaging system can be used for both planning treatment and subsequently used during treatment. The X-ray imaging system is preferably a high resolution imaging system that can create images using CT reconstruction techniques, as well as stationary and scout views. Preferably, the stationary and scout views can be stereoscopic views for determining the position of the target region relative to and/or within a region of interest.

Figure 1:
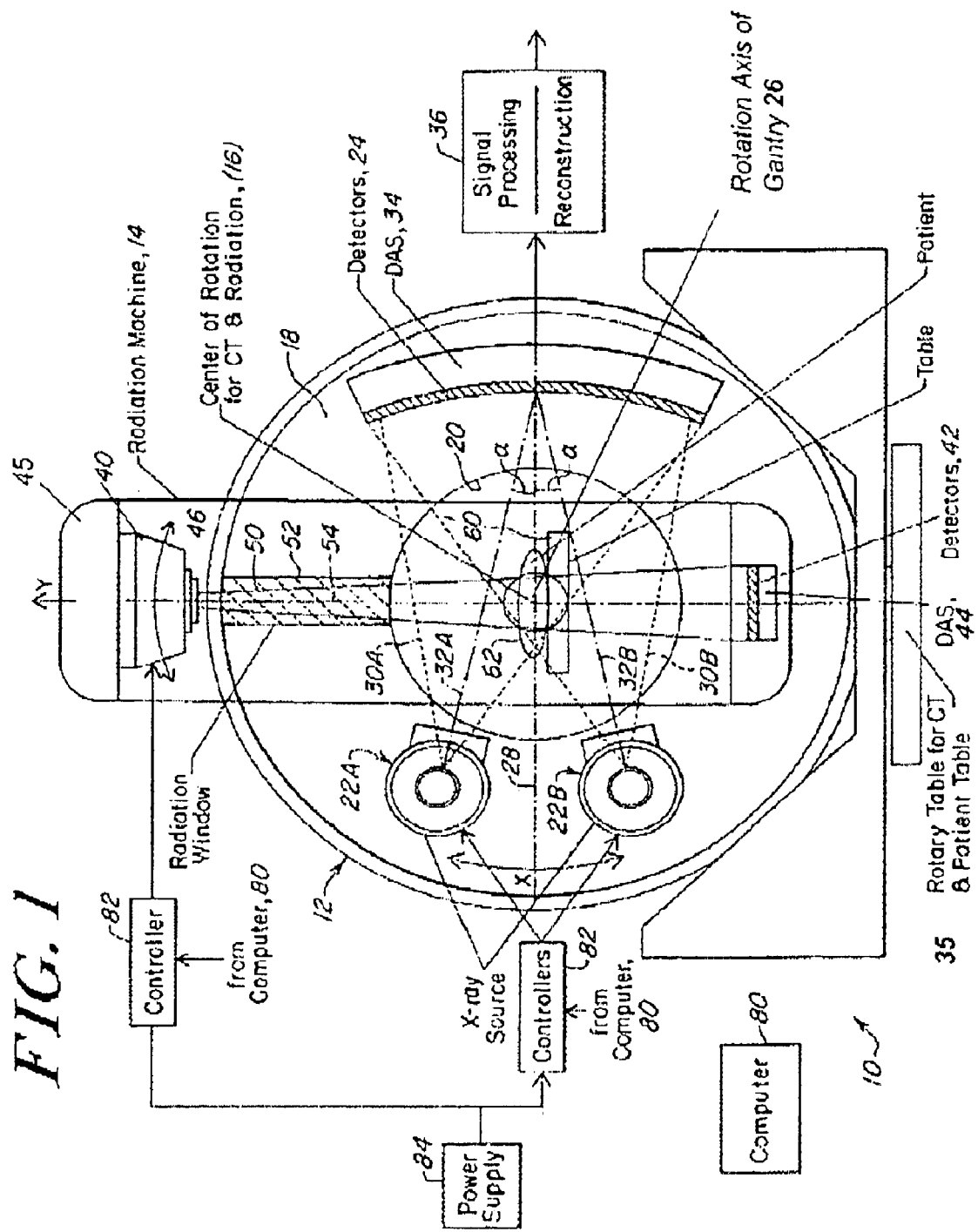
FIG. 1 shows an end view of a system for imaging a target region and treating the region with radiation therapy.
Figure 2:
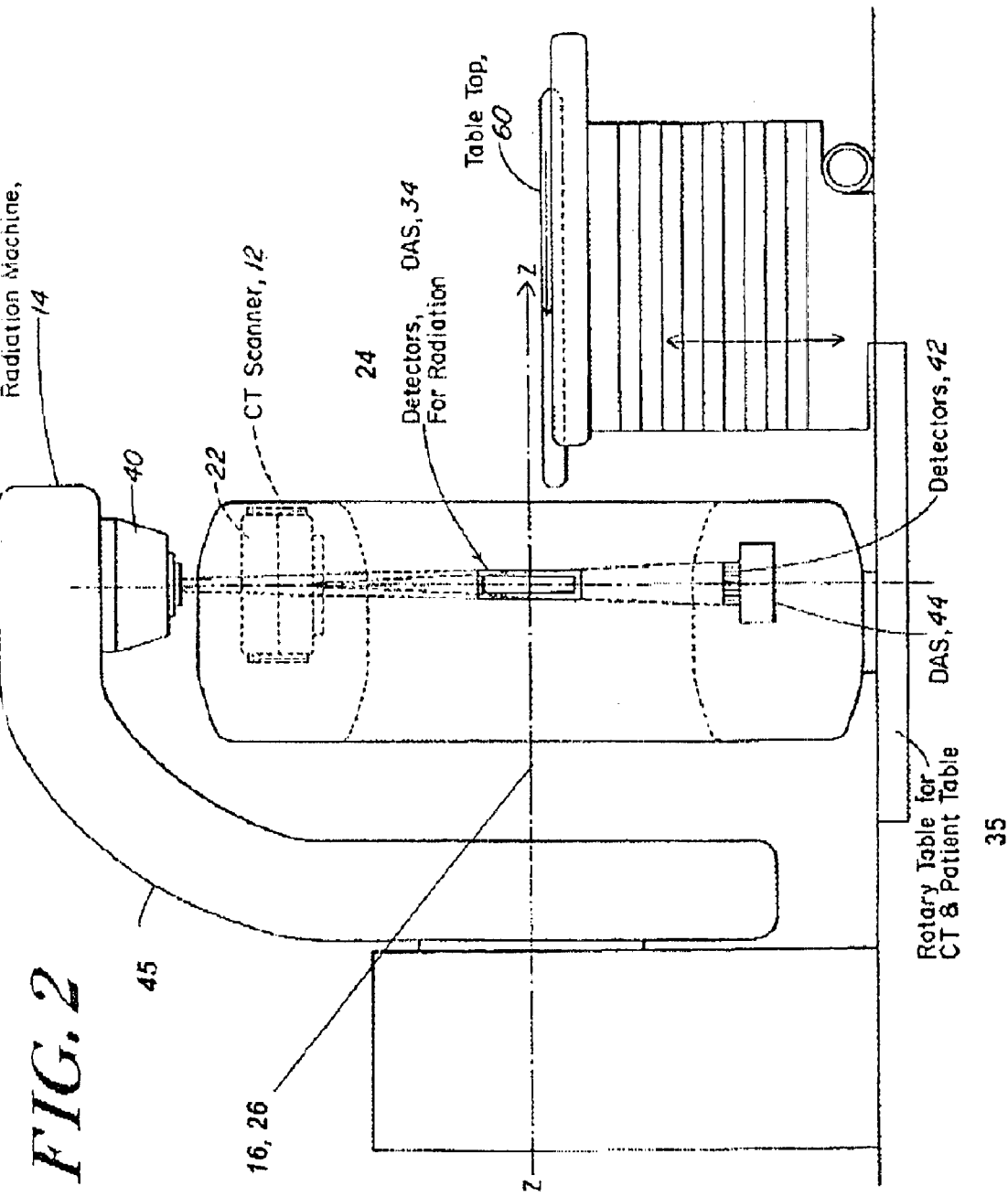
FIG. 2 shows a cross sectional side view of the system shown in FIG. 1 taken along line 1—1.

The preferred system is shown in FIGS. 1 and 2. In the system 10, the CT imaging subsystem 12, and the therapy radiation subsystem 14 are mounted for rotation about the same isocenter 16.

The imaging system 12 includes a rotatable gantry 18 having a patient aperture 20. A pair of X-ray sources 22A and 22B (or moving electron beam source) and a detector array 24 are fixedly mounted on the gantry 18 to rotate with the gantry around the isocenter 16 about a rotation axis 26 (defining a z-axis seen in FIG. 2). The sources 22 are positioned almost diametrically opposite the detector array 24 on opposite sides of a bisector 28 passing through the isocenter 16 and the geometric center of the array 24 such that an imaging x-ray fan beam 30A (or 30B) of each source is emitted from the source toward the detector array 24 along a center line 32A (or 32B), displaced by an angle α relative to a bisector 28. In addition, the sources 22 can be fixed relative to the detector array 24 such that the imaging x-ray fan beams 30A and 30B are shifted ¼ of the detector pitch. In FIG. 2, the x-ray source 22 is shown in broken lines simply to illustrate that it is movable with the gantry 18. The x-ray source 22 and the detector array 24 are normally located across from one another on the gantry 18.

The detector array 24 includes one or more rows of detectors suitably connected to a data acquisition system (DAS) 34, which in turn is connected to suitable components used in CT scanners (indicated at 36) so as to form image data of one or more slices respectively through one or more slice planes passing though at least a portion of the patient's body positioned in the patient aperture 20 within a region of interest, referred to as the field of view.

In addition, the radiotherapy subsystem 14 is preferably positioned to pivot about the same Z-axis and isocenter 16. The therapy radiation subsystem 14 includes a high energy X-ray source 40 and one or more high energy detectors 42. As shown the source 40 is mounted on a pivotal support such as a C-arm 44, while the high energy detectors 42 are mounted on the gantry 18. Alternatively, the high energy detectors 42 can be spatially fixed with respect to the source 40 so as to be positioned diametrically opposite the source 40 at all times. The output of the detectors 42 can he provided to a separate data acquisition system (DAS) 44. A suitable collimator subsystem (including for example, one or more known multi-leaf collimators) is provided at 46 so that the cross-sectional shape and size of the radiotherapy beam used to expose the target region of the patient can be modified depending upon the cross-sectional size and shape of the target region at the angle of the exposure by the source 40. The source 40 and detectors 42 are preferably, although not necessarily mounted so that when the detectors 42 are positioned diametrically opposite the source 40 (relative to the isocenter) the center axis of the high energy radiotherapy beam 50 emitted from the source 40 toward the detectors 42 is aligned with (i.e., the center axis 54 of the beam 50 is contained within) a region of interest (the latter defining a radiation window 52) within the slice plane of the imaging system 12. Thus, the axis 54 of the beam 50 preferably lies within the slice plane. The Although not shown, the support 44, and thus the source 40, of radiotherapy subsystem 14 can be made to be pivotal about a substantially horizontal axis (indicated as the X-axis in FIG. 1) passing through the isocenter 16 preferably, although not necessarily, through at least 180 degrees. This allows the radiation window 52 to also pivot. Alternatively, the detectors 42 can be secured to the same support as the source 40 so that the two always remain diametrically opposed to one another about the isocenter 16 of the machine, and pivot together about the X-axis of the machine. In this ease the detectors 42 tire mounted so as to be clear the gantry.

Finally, a table 60 is provided for supporting the patient 62. The table 60 is adapted to move in the Z-axis direction (shown in FIG. 2) as well as the Y direction, i.e., up and down, and preferably also the X direction, i.e., left and right as shown in FIG. 1, all within the region of interest in the slice plane.

The imaging subsystem 12 can be used in the planning stage using standard CT techniques by positioning the patient on table 60 in the aperture 20 with the target region position close to the isocenter 16. When using the imaging system one or both of the X-ray sources 22A and 22B can be used. With one source 22 the chosen source is used to emit the X-ray beam 30 toward the detector array 24 as the source and array rotate about the rotation axis 26. Similarly, both X-ray sources can be used to acquire CT data. In this latter case, the X-ray sources can share the detectors of the array 24 by being alternatively switched so that when one X-ray source is emitting X-rays, the other is not. By switching back and fourth at a high rate, the amount of data provided by the detector array from each source can be utilized.

Each of the sources can provide a single energy beam or a dual energy beam (by being alternatively switched) for improved scanning imaging results.

Figure 3:
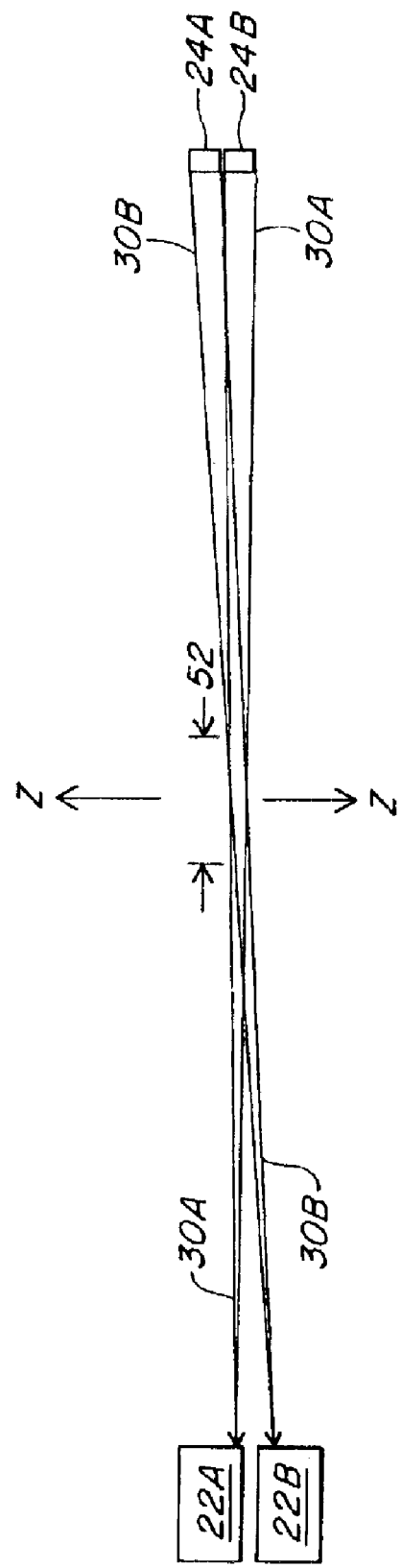
FIG. 3 shows a schematic diagram illustrating one embodiment of a two sources and detector arrays to provide dual energy imaging.

Alternatively, as shown in FIG. 3, each source 22A and 22B may be offset along the Z-axis direction and the array of detectors can include two rows 24A and 24B, one for each source. In this arrangement data acquired from each row is acquired from exposure from a different source, and separate sets of data can be acquired using the two sources at the same time. The imaging fan beam emitted from each source preferably intersect in the area of interest, which is preferably the area represented by the radiation window 52 defined by the radiotherapy subsystem.

When using both sources 22A and 22B to acquire CT data, dual energy imaging techniques can be employed with one source providing a high energy imaging beam and the other a low energy imaging beam; or where the two sources provide imaging beams to separate rows of detectors, they each can be single energy or dual energy for improved scanning imaging results.

Multiple sliced images can be obtained by moving the patient table 60 in increments in the Z-axis direction so that images can be made of the target region of the patient 62 and its surrounds. These images can be used to plan treatment with the radiotherapy subsystem 14.

When treatment is to be provided the patient 62 is positioned on table 60 in the aperture 20 with the target region once again near the isocenter 16, reasonably close to the region of interest defining the radiation window 52. The imaging subsystem 12 can then be used as a CT scanner to take multiple slices of the patient and compared, if necessary to the sliced images taken during the planning stage. The comparison can be done automatically, or compared by the user.

Once the shape, size and location of the targeted region is initially determined, the table is moved to insure that the targeted region of the patient is within the region of interest so that it can be exposed to the radiotherapy beam 50. Then high energy x-ray treatment can begin. The therapy radiation machine can be rotated though a number of positions that align the radiotherapy beam 50 with the target region, the collimator adjusted to the appropriate size and shape from that direction and the target region exposed to the radiation. The therapy radiation machine is then moved to another angular position, and the location of the target region determined to insure that the therapy radiation beam is shaped, sized and properly aligned with the targeted region prior to exposure.

During the radiotherapy phase of treatment it should be appreciated that the imaging system need not utilize full CT images to locate the target regions and move the patient table to insure the targeted region is in the region of interest so as to be exposed to substantially all of the exposed radiation passing though the body. Instead the gantry 18 may be maintained in a fixed or stationary view prior to the exposure by the radiotherapy beam. Both X-ray sources 22A and 22B can be used to expose the region of interest for creating views. The two images can be taken sequentially, when the sources share the same detector array, or simultaneously, where each source emits X-rays to its own row of detectors as shown, for example, in FIG. 3. The two images can them be combined to provide a stereoscopic image, wherein the location of the target region can be determined.

Once the target region is determined from a particular location, the appropriate adjustments to the size and shape of the radiotherapy beam can be made and the region exposed.

Where the target region is not precisely aligned with the radiotherapy beam, the table can be adjusted to move the patient to insure the proper positioning (in the x, y and/or z directions). Alternatively, once the target region is determined to be in the proper position in the z direction, the angular position of the radiation source 40 of the radiotherapy machine 14 can be rotated to the proper orientation to insure that the radiotherapy beam is directed and shaped to match the targeted region.

All of this exposure process can be done automatically, with some or complete control by the therapist, by using a computerized system including a computer 80, controllers 82 for controlling the power supplied by the supply 84 to the sources 22A, 22B and 40, as well as processing the data acquired during the planning and treatment phases. Further the computerized system can automate the comparison of images taken during both phases to insure and maximize treatment.

Finally, the detector array 42 can measure and help control the dose of each exposure, an improvement over the current use of film. The output of the data acquisition system 44 can be used by the therapist to insure proper doses and exposure of radiation are being administered.

The invention may be embodied in other specific forms without departing from the spirit or central characteristics thereof. The present embodiments are, therefore, to be considered in all respects as illustrative and not restrictive, the scope of the invention being indicated by appending claims rather than by the foregoing description, and all changes that come within the meaning and range of equivalency of the claims are therefore intended to be embraced therein.

What is claimed is:

1. A combined system for planning and delivering X-ray therapy to a patient, the system including:

a CT imaging subsystem defining at least one slice plane so that data generated by the CT imaging subsystem can be used to create images relative to the slice plane so that a target region of the patient can be (a) determined for treatment during a planning phase and (b) imaged during treatment during a treatment phase, wherein the CT imaging subsystem includes at least two sources of X-rays; and a radiation therapy subsystem including a source for delivering a beam of therapeutic X-rays to the target region of the patient during treatment;

wherein the radiation therapy subsystem provides the beam of the therapeutic X-rays in a direction which is in a plane that is substantially fixed relative to the slice plane of the CT imaging subsystem and substantially coplanar with the slice plane of the CT imaging subsystem so that the targeted region can be imaged, and exposed to the beam of therapeutic X-rays without the necessity of moving the patient.

2. A system according to claim 1, wherein the radiation therapy subsystem includes a detector for detecting the radiation level of the beam.

3. A system according to claim 1, wherein the radiation therapy subsystem includes a collimator subsystem for shaping and sizing the beam of therapeutic X-rays.

4. A system according to claim 1, wherein the radiation therapy subsystem includes a support for pivoting a source of the beam of therapeutic X-rays so that the beam can be directed from a predetermined angle.

5. A system according to claim 4, wherein the CT imaging subsystem is adapted to provide stationary views.

6. A system according to claim 1, further including a subsystem for automatically comparing images created during the planning and treatment phases.

7. A system according to claim 1, further including a patient table for use in both the planning and treatment phases.

8. A system according to claim 7, wherein the table is adjustable in three orthogonal directions.

9. A combined system for planning and delivering X-ray therapy to a patient, the system including:

a CT imaging subsystem defining at least one slice plane so that data generated by the CT imaging subsystem can be used to create images relative to the slice plane so that a target region of the patient can be (a) determined for treatment during a planning phase and (b) imaged during treatment during a treatment phase, wherein the CT imaging subsystem includes two sources of X-rays and is programmed and adapted to use the two sources to create a stereoscopic image of the target region; and a radiation therapy subsystem including a source for delivering a beam of therapeutic X-rays to the target region of the patient during treatment, wherein the radiation therapy subsystem provides the beam of the therapeutic X-rays in a direction which is in a plane that is substantially fixed relative to the slice plane of the CT imaging subsystem so that the targeted region can be imaged, and exposed to the beam of therapeutic X-rays without the necessity of moving the patient, wherein the radiation therapy subsystem includes a support for pivoting a source of the beam of therapeutic X-rays so that the beam can be directed from a predetermined angle and the CT imaging subsystem includes at least two sources of X-rays or a moving electron beam source.

10. A system according to claim 9, wherein the CT imaging subsystem is programmed and adapted to use the two sources to create a three-dimensional image of the target region.

11. A system according to claim 9, wherein the CT imaging subsystem is programmed and adapted to use the two sources to create separate images of the target region.

12. A system according to claim 9, wherein the CT imaging subsystem is programmed and adapted to use the two sources to create dual energy beams of X-ray radiation.

13. A method of locating a targeted region in a patient using a CT imaging subsystem, and treating the targeted region with therapeutic X-ray radiation using a radiotherapy subsystem, comprising:

providing the therapeutic X-rays in a direction within a plane which is substantially fixed relative to a slice plane of the CT imaging subsystem and substantially coplanar with the slice plane of the CT imaging subsystem so that the targeted region can be imaged during a planning phase, and imaged and exposed to the therapeutic X-rays during a treatment phase without the necessity of moving the patient, wherein the CT imaging subsystem includes at least two sources of X-rays.

14. A method according to claim 13, further including detecting the radiation level of the beam with a detector subsystem.

15. A method according to claim 13, further including adjusting the shape and size of the beam of therapeutic X-rays with a collimator subsystem.

16. A method according to claim 13, further including pivoting a source of the beam of therapeutic X-rays so that the beam can be directed from a predetermined angle.

17. A method according to claim 16, further including forming stationary views with the CT imaging subsystem during the treatment phase.

18. A method according to claim 13, further including automatically comparing images created during the planning and treatment phases.

19. A method according to claim 13, further including using a patient table for both the planning and treatment phases.

20. A method according to claim 19, further including adjusting the table, as necessary in each of three orthogonal directions.

21. A method of planning and delivering X-ray therapy to a patient, comprising:

defining at least one slice plane of a CT imaging subsystem so as to create images relative to the slice plane so that a target region of the patient can be (a) determined for treatment during a planning phase, and (b) imaged during treatment during a treatment phase, using at least two sources of X-rays;

delivering a beam of therapeutic X-rays to the target region of the patient during the treatment phase;

wherein the beam of the therapeutic X-rays is delivered in a direction which is in a plane that is substantially fixed relative to the slice plane so that the targeted region can be imaged, and exposed to the beam of therapeutic X-rays without the necessity of moving the patient;

pivoting a source of the beam of therapeutic X-rays so that the beam can be directed from a predetermined angle; and further including using the two sources to create stationary views of the target region and create a stereoscopic image of the target region.

22. A method according to claim 21, further including using the two sources to create separate images of the target region during the planning phase.

23. A method according to claim 21, further including creating dual energy beams using the two sources.

* * * * *